United States Patent [19]

Hasslinger

[11] Patent Number: 4,569,348
[45] Date of Patent: Feb. 11, 1986

[54] CATHETER TUBE HOLDER STRAP
[75] Inventor: Russell Hasslinger, Wyckoff, N.J.
[73] Assignee: Velcro USA Inc., Manchester, N.H.
[21] Appl. No.: 123,783
[22] Filed: Feb. 22, 1980
[51] Int. Cl.⁴ ............................................. A61M 25/02
[52] U.S. Cl. .................................. 604/179; 24/16 R;
128/DIG. 15; 128/DIG. 24
[58] Field of Search .............. 128/348, 165, DIG. 26,
128/349 R, 132, 133, 134, 351, 350 R, 171,
DIG. 15; 224/208, 902; 24/16 R, 73 CC, 73
GS, 73 SA, 81 CC

[56] References Cited
U.S. PATENT DOCUMENTS

| | | | |
|---|---|---|---|
| 3,000,384 | 9/1961 | Piers, Jr. | 132/46 R |
| 3,288,136 | 11/1966 | Lund | 128/348 |
| 3,297,026 | 1/1967 | Van Pelt | 128/165 |
| 3,726,280 | 4/1973 | Lacount | 128/DIG. 26 |
| 3,834,380 | 9/1974 | Boyd | 128/DIG. 26 |
| 3,878,849 | 4/1975 | Muller et al. | 128/DIG. 26 |
| 4,018,221 | 4/1977 | Rennie | 128/DIG. 26 |
| 4,088,136 | 5/1978 | Hasslinger et al. | 128/DIG. 26 |
| 4,090,508 | 5/1978 | Gaylord, Jr. | 128/165 |
| 4,096,863 | 6/1978 | Kaplan et al. | 128/DIG. 26 |
| 4,142,527 | 3/1979 | Garcia | 128/348 |
| 4,243,028 | 1/1981 | Puyana | 128/165 |

Primary Examiner—Paul J. Hirsch
Attorney, Agent, or Firm—Pennie & Edmonds

[57] ABSTRACT

A separable fastening device is disclosed to support a medical device such as a catheter tube or the like to a limb of a patient. The device includes a first and a second strap member. The first strap member includes a flexible first strap section formed of a knitted textile material having upstanding from one surface a plurality of multifilamentary loop-like elements and a polyurethane foam substrate secured to the opposite surface. The first strap member also includes a second strap section which is formed of a flexible tape member having upstanding from one surface a plurality of hook-like elements which matingly engage with the upstanding filamentary loop-like elements of the first section so as to be attachable thereto at the respective end portions to form a complete flexible first strap member. The second strap member includes a third strap section formed of a flexible tape member having an adhesive coating on one surface and a plurality of hook-like engaging elements on the opposite surface. The adhesive surface can be wrapped about the catheter tube and thereafter the hook-like elements can be matingly engaged with the loop-like elements of a portion of the first strap section. Upon encircling the first strap section about a limb and enfolding it over the third strap section, the hook-like elements of the second strap section can matingly engage the loop-like elements of the first strap section to secure the catheter tube in relation to the limb.

27 Claims, 9 Drawing Figures

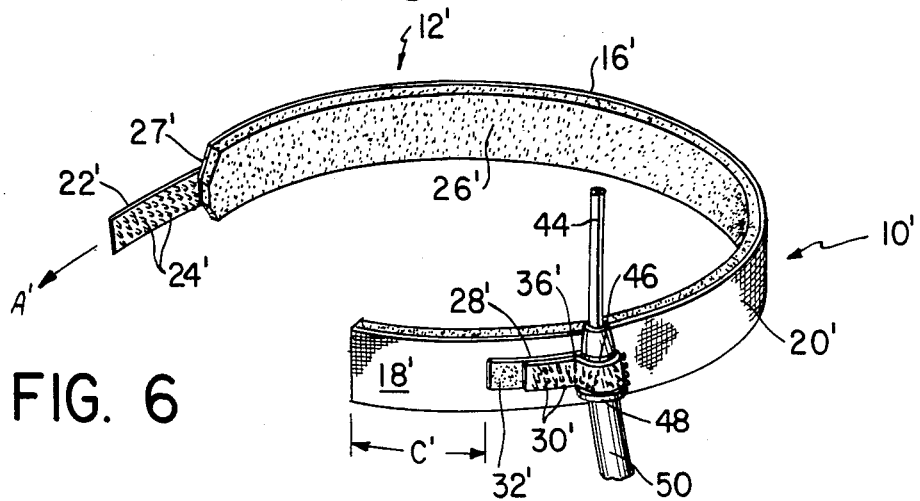
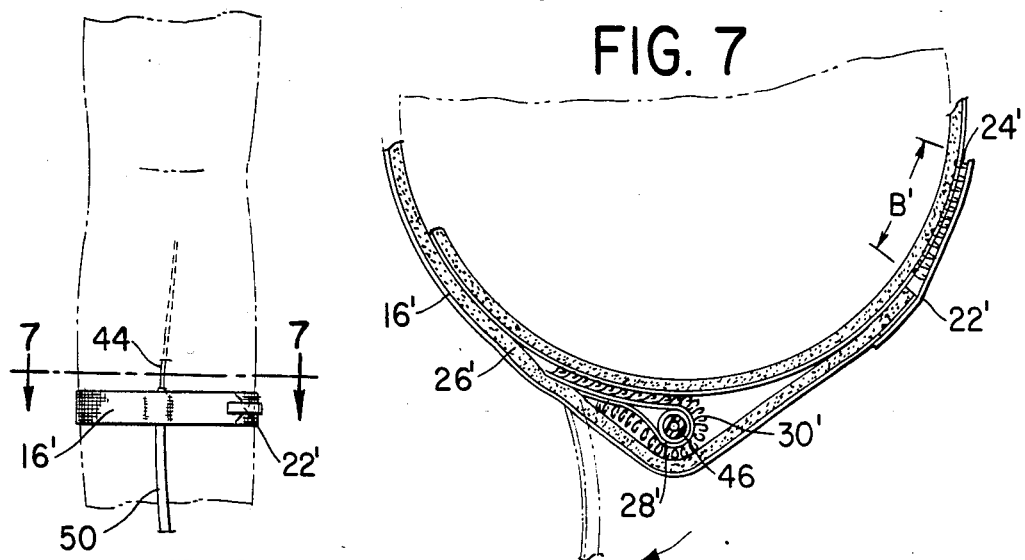
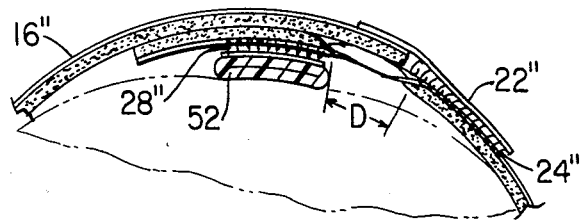

CATHETER TUBE HOLDER STRAP

TECHNICAL FIELD

This invention relates to a separable fastener which is in the form of a strap member for encompassing and supporting members such as medical tubes, and more particularly to a separable fastener for supporting a catheter tube to a body portion.

BACKGROUND ART

Separable fasteners such as those described in U.S. Pat. Nos. 2,717,437 and 3,009,235 which are marketed under the registered trademark VELCRO ® brand hook and loop fasteners by Velcro USA, Inc., 521 Fifth Ave., New York, N.Y. have gained wide acceptance because of the properties of the mating hooks and loops. A surface defined by the hooks is merely placed into face-to-face relationship with a surface defined by the loops so that a large number of hooks engage a large number of loops and therefore are able to resist separation by forces parallel to the interfacial plane of engagement but are readily separable by peeling forces applied substantially normal to this interfacial plane. These fastening devices are generally formed of a sheet of synthetic woven or knitted fabric having raised threads of synthetic material, such as nylon, which are napped or unnapped to provide a pile surface defined by a plurality of loops, and which may be thermally treated to become semi-rigid. certain of the loops may then be cut along one side near their outer extremity to form hooks.

These fasteners have been utilized in numerous applications in many fields of use, particularly because of their unique touch and close fastener capability as well as their fastening strength. The unique fastening capability of these hook and loop-type engaging elements have been applied to particular uses to create new and unobvious fastener arrangements.

In particular, fasteners of this type have previously been utilized either alone or as major components of strapping devices of various types. Although the prior art dealing with straps and the like includes numerous fastener devices of various types to secure the straps in their intended environment, the applications of these separable hook and loop-type fasteners have reduced the need for the traditional strap fastening devices such as buckles and the like. To the extent that the early fastening devices did not generally facilitate variable and precise fastening, the application of these separable fasteners to the strap art has proven to provide substantial advantages.

U.S. Pat. No. 3,000,384 to Piers, Jr., relates to a fastener tie to retain a hank or lock of hair in a desired shape. In an embodiment, a portion of longitudinally elastic tape is threaded through the opening of an attached elongated eye in such a way that the tape forms a spiral-like configuration. U.S. Pat. No. 3,297,026 to Van Pelt, relates to a restraining device for holding a limb of an anatomical body. The restraining device includes an elongated resilient pad wrapped around a part of a human limb. U.S. Pat. No. 3,726,280 to Lacount relates to a catheter support combining VELCRO ® brand fasteners with an elastic band which is secured around the patient's thigh. U.S. Pat. No. 3,827,107 to Moore, relates to an adjustable strap assembly which utilizes VELCRO ® brand fasteners in combination with a pad having hooking elements on both sides to eliminate the requirement of an excessively long length of looped strap portion. U.S. Pat. No. 3,878,849 to Muller et al., relates to a surgical tube supporter having an elastic strap with a high friction layer on one face to engage the patient's skin. In still another development, a strap adapted to support surgical tubes is comprised of an elastic strap portion connected at one end to an inelastic strap portion with hook and loop-type fastener tape members attached thereto to the interface between the elastic and inelastic strap portions. An endless ring-like member is utilized to loop the hook fastener tape about the surgical tube to provide support therefore.

A catheter tube holder is disclosed in commonly assigned U.S. Pat. No. 4,088,136. The construction of the tube holder utilizes a VELFOAM ® brand strap material, i.e., foam material having a loop material backing bonded thereto. The catheter tube is secured snugly by the end portion of a strap section by folding the strap portion about the tube and inserting it into an opening adjacent an end thereof so as to secure the tube inside the strap. While this tube holder represents a significant improvement in such devices, the invention of the present application provides significantly improved securement of a first member such as a catheter tube to a second member such as a limb of a patient in a manner not previously attainable.

Along with the fastening advantages of the prior art, certain disadvantages nevertheless remain, particularly when the fastener device is utilized to support a catheter strap to a patient's limb. For example, in the presently known devices, which utilize elastic bands and the like, there is a tendency to restrict the flow of blood through the encircled human limb and this constriction has been known to cause ulcerations of the limb. Still others neither firmly support and secure the catheter tube to the strap nor the strap to the limb and this failure generally results in pain and discomfort to the patient if the tube slips out of position or becomes otherwise relocated. In addition, the prior art devices do not provide a strap of a fixed length which may be varied in size to accommodate limbs or body portions of numerous sizes. We have invented a relatively inexpensive fastening device in which these disadvantages are successfully avoided and which is particularly useful in providing generally firm but gentle support for catheter tubes and the like.

DISCLOSURE OF THE INVENTION

The invention relates to a separable fastening device adapted to support a first member on a second member. The fastening device comprises a first strap section having a plurality of engaging elements upstanding from a first surface thereof. A second strap section is connected to and extends from the first strap section and has a plurality of mating engaging elements upstanding from a surface opposed to the first surface of the first strap section. The second strap section is capable of being positioned opposite the first surface of the first strap section such that the respective mating engaging elements may be placed in mating engaged face-to-face relation. The fastening device also comprises a third strap section having adhering means on a first surface portion thereof and a plurality of engaging elements upstanding from an opposite surface thereof. The third strap section is capable of being positioned in mating engaged relation with the engaging elements of the first surface of the first strap section. The third strap section is dimensioned such that the adhering surface can be positioned in engaged adhered relation with at least a portion of the surface of the first member and adhered thereto so as to securely encompass at least a part thereof such that the first strap section may be positioned about the first member and the third strap section and the respective mating engaging elements placed in engaged relation so as to support the first member on the second member.

In a preferred embodiment, the separable fastening device adapted to support a first member such as a catheter tube or the like on a second member comprises a first and a second strap member. The first strap member includes a first flexible strap section having a plurality of engaging elements upstanding from a first surface thereof. The first strap member also includes a second flexible strap section connected to and extending from the first strap section and having a plurality of mating engaging elements upstanding from a surface opposed to the first surface of the first strap section. The second strap section is capable of being positioned opposite the first surface of the first strap section such that the respective mating engaging elements may be placed in mating engaged face-to-face relation. The second strap member includes a third strap section having adhering means on a first surface portion thereof and a plurality of engaging elements upstanding from an opposite surface thereof and capable of being positioned in mating engaged relation with the engaging elements of the first surface of the first strap section. The third strap section is dimensioned such that the adhering surface can be positioned in engaged adhered relation with at least a portion of the surface of the first member and adhered thereto so as to securely encompass at least a part thereof such that the first strap section may be positioned about the first member and the third strap section and the respective mating engaging elements placed in engaged relation so as to support the first member on a second member.

Although the first strap member of the separable fastening device may be of a unitary construction, preferably it and the second strap member are constructed of VELCRO ® brand separable fastener tape materials suitably secured to each other to provide the desired arrangement. The separable fastener tape may have a base member, woven or knitted of a synthetic heat deformable material such as nylon, polyester, and the like, having resilient engaging elements upstanding from the respective base member. In the present embodiment, the engaging elements are constructed in the form of hook-type hooking elements which can mate with loop-type hooking elements on opposed engaging surface portions. However, it should be understood that any flexible engaging elements, including mushroom-like elements, resilient projections, etc., which are readily securable in face-to-face relation, and which particularly resist forces parallel to the interfacial plane of engagement, are contemplated within the scope of the present invention, provided the fastener strap is flexible. Such mushroom configured hooking elements of the type disclosed in U.S. Pat. Nos. 3,138,841 and 3,320,649 both to Naimer, and U.S. Pat. Nos. 3,718,725 and 3,770,359 both to Hamano are contemplated. Further examples of knitted form fastener members contemplated within the scope of the present invention are disclosed in U.S. Pat. Nos. 3,530,687 and 3,539,436 both to Hamano.

In the preferred embodiment, the first strap section is comprised of a strip of knitted textile material made from nylon multifilamentary yarns and constructed to have a multiplicity of loop-type filamentary engaging elements upstanding from a surface of the textile material. Also, a polyurethane foam material substrate is preferably secured to the opposite surface of the textile material. The advantages of a strap section having such a foam material substrate are numerous. For example, when a portion of the foam material is looped about an elongated member such as a catheter tube and positioned in supporting relation therewith, the foam provides a soft, but firm non-slip support for the catheter tube and does not constrict the flow of fluids through the tube. Consequently, when the foam material is placed in encompassing relation about a human limb its frictional resistance and stretchability are such as to firmly secure the tube to the strap and the strap to the limb. The cushioning characteristics of the foam material uniquely prevents the constriction of blood through the encompassed limb while simultaneously providing the necessary support for the tube. Since the porosity of the foam material allows air to circulate therethrough to the limb, it also prevents excoriation (chafing) of the skin. The foam material textile combination contemplated in the preferred embodiment is a strap material of approximately ¼ inch thickness and is marked by VELCRO USA, Inc. under the registered trademark VELFOAM ®.

In its preferred form, the second strap section is comprised of a fastener tape having on one surface a multiplicity of hook-type engaging elements for matingly engaging the upstanding multifilamentary loop-type engaging elements of the first strap section so as to securely retain the catheter tube which is enveloped within overlapping portions of the first strap section.

The catheter tube is initially encompassed by a third strap section which is similar to the construction of the second strap section except that it additionally has an adhesive coating, preferably pressure-sensitive on the non hook-type engaging surface. By utilizing a pressure-sensitive adhesive, the third strap section can be provided with a removable release paper. By means of this adhesive coating, the third strap section can be positioned over and adhered to at least a portion of the surface of the catheter tube. Since the catheter tube typically is substantially made of silicone which presents a low friction surface when in contact with most other materials, the adhesive permits the catheter tube to be secured to the third strap section in a fixed relationship. In this manner, rotation and slippage of the catheter tube is avoided. Preferably the third strap section is of a sufficient size so that portions of the adhesive coated surface which do not encompass the tube can be adhered to each other. In turn, the third strap section can then be attached to the loop-type engaging surface of the first strap section. Overlapping portions of the first strap section as it is wrapped around a body limb or portion envelope the third strap section therebetween and thereby the catheter tube. In an alternative embodiment, the first strap section can be folded by twisting back onto itself before and after the portion of the first strap section enveloping the third strap section and thereby the catheter tube.

In an alternative embodiment, the third strap section has a polyurethane foam material substrate secured to the non-hook surface of the textile material of the respective fastener tape. In this case, the adhesive coating is placed on the free surface of the foam material which offers the advantages noted above with respect to the foam material of the first strap section.

Although the hook and loop-type fastener tapes permit adjustability in the size of the strap, the combination of knitted textile fabric and foam material may be readily severed to permit the creation in-situ of several sizes which may accommodate human limbs of various proportions. Thus, a single length fastener may be provided for virtually all limb sizes, taking into consideration, not only the variations from person to person, but also the variations from legs to arms, etc.

It will be further appreciated that the inventive separable fastening device provides a relatively inexpensive, washable, autoclavable device, and these features are particularly significant when it is constructed to support medical devices such as catheter tubes of all types, particularly Foley Catheters.

It will be further appreciated that in its broadest application, the invention is nevertheless extremely useful for supporting, securing or connecting any object or device to another member or to a frame structure, beam and the like.

BRIEF DESCRIPTION OF THE DRAWINGS

Preferred embodiments of the invention are described hereinbelow with reference to the drawings wherein:

FIG. 5 is a perspective view of the separable fastening device of the invention for use in supporting an intravenous tube to a body portion of a patient;

FIG. 6 is a view of a patient's limb, illustrating the use of the device of FIG. 5 for supporting an intravenous tube to a patient's arm;

FIG. 7 is a view, partially in cross-section and partially cut-away, taken along lines 7—7 of FIG. 6; and FIG. 8 is a view, partially in cross-section and partially cut-away, of the separable fastening device of the invention illustrated for use in supporting an EKG electrode pick-up to a body portion of a patient.

BEST MODE FOR CARRYING OUT THE INVENTION

For the purpose of the description which follows, the references to fastener tapes having "hook-type hooking elements" and "loop-type hooking elements" contemplate all such separable fastener tapes of the "press to close, peel to open" type. For example, engaging elements of the loop-type may include filamentary hooking elements upstanding from a surface of the fastener tape, as well as engaging elements in the form of loops per se upstanding from such tapes. Further, hooking elements of the hook-type, contemplate such engaging elements as mushroom, burrs and the like, as well as hooks per se upstanding from a surface of the fastener type.

Figure 1:
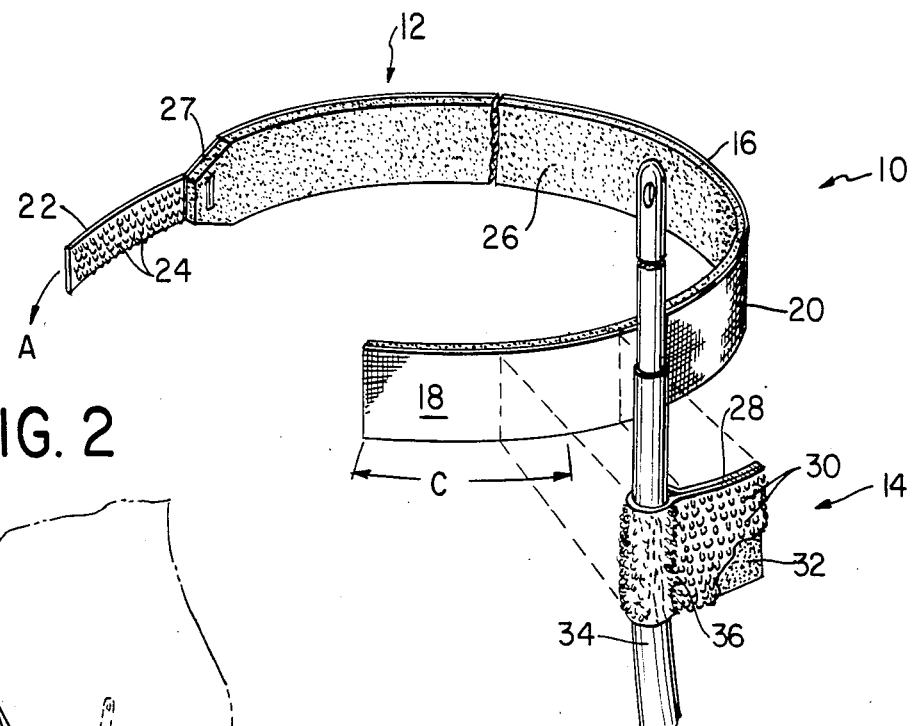
FIG. 1 is a view illustrating the separate components of a separable fastening device of the present invention.

Referring to FIG. 1, there is illustrated a separable fastening device 10 in the form of a first strap member 12 and second strap member 14. The first strap member 12 comprises a first strap section 16 having a knitted fastener tape 18 and a plurality of resilient loop-type hooking elements 20 upstanding from one surface of the fastener tape 18. The first strap member 12 also comprises a second strap section 22 having a plurality of mating hook-type hooking elements 24 upstanding from a surface thereof which is positioned opposite to the loop-type hooking surface of tape 18 of the first section 16. The first and second strap sections 16, 22 may be entirely integrally constructed or connected by sewing, welding, gluing, etc. In the preferred form, they are attached to each other as shown by pressing the mating surfaces of two respective end portions together and securing them together by ultrasonic welding. The knitted loop fastener tape 18 is preferably of the type marketed by VELCRO, USA, Inc. under the trade name "V22-70" and is attached at one end to a separate length of VELCRO ® brand hook fastener tape 22 such that the hook-type hooking elements 24 of the other tape 22 face in the opposite direction relative to the loop-type hooking elements 20.

Referring further to the drawings, the VELCRO ® brand hook fastener 22 has a woven nylon base and resilient hooking elements 24 upstanding therefrom. The loop fastener tape 18 of the first section 16 consists of a tricot knit nylon textile material having a plurality of nylon multifilaments 20 upstanding from one surface. The nylon multifilaments are formed by a plurality of multifilamentary yarns which are interknitted into the base member with floating stitches and the material is thereafter brushed or napped to cause the multifilamentary yarns to stand and appear as a fuzzy, pile surface which has been found to conveniently engage the VELCRO ® brand hook fastener tape in a manner similar to the engagement with VELCRO ® brand woven loop material. While this filamentary brushed suface does not provide the same holding power as VELCRO ® brand fastener tape (i.e. having actual loops upstanding from one surface), it is relatively inexpensive to manufacture and its knitted character has been found to provide holding capability which is sufficient for use in supporting numerous types of medical devices as will be seen in the description as it develops. In fact, less holding power is more desirable for securing medical devices to patients, particularly those in pain, since the components of the fastening device 10 may be readily separated without cause of pain or discomfort to the patient.

Referring once again to FIG. 1, first strap section 16 is constructed of a layer of polyurethane foam material 26 secured by flame lamination to the base of the VELCRO ® brand V22-70 loop fastening tape 18. The combination of multifilamentary yarn material V22-70 with the polyurethane foam material is a stretchable foam backed material known as VELFOAM ® having somewhat elastic properties and is commercially available through the VELCRO ® brand fastener tape distribution system.

The first strap section 16 has a tapered end portion 27 which tapers to a width having a dimension comparable to that of second strap section 22. The tapered end portion is preferred over a rectangular end portion (not shown) since the corners of the last mentioned configuration could catch on other objects and thereby possibly result in separation of the strap sections of the fastening device 10. In addition, the tapered configuration facilitates continued attachment of the strap sections once positioned in a secured relationship as shown in FIGS.

Figure 2:
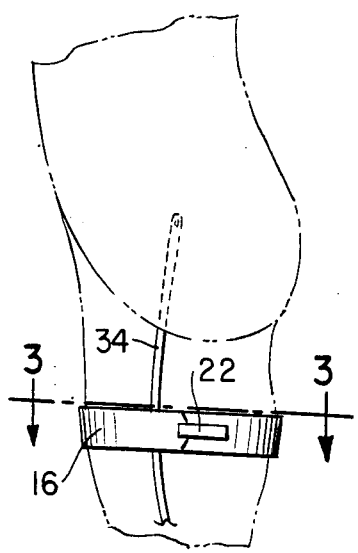
FIG. 2 is a view illustrating the use of the separable fastening device of FIG. 1 as a catheter tube support.
Figure 3:
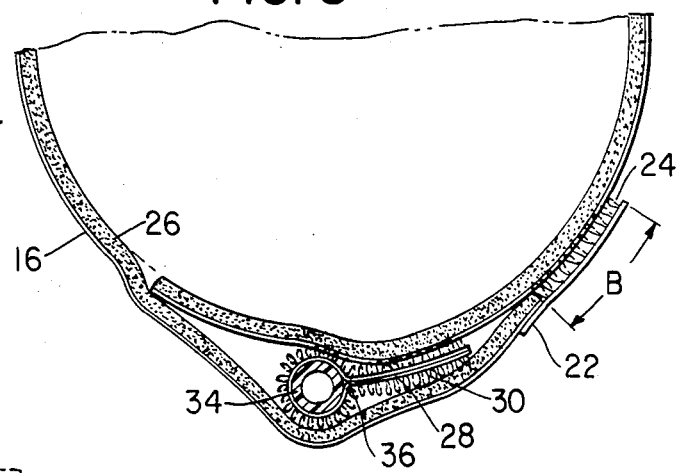
FIG. 3 is a view partially in cross-section and partially cut-away, taken along lines 3—3 of FIG. 2.

2 and 3. The strap sections 16 and 22 are suitably sized so that strap section 16 can be encircled in the direction of arrow "A" (shown in FIG. 1) about a limb of a patient such as a leg, while strap section 22 can extend or fold over strap section 16 as shown in FIGS. 2 and 3.

The second strap member 14 includes a third strap section 28 which, like the second strap section 22, has a plurality of mating hook-type hooking elements 30 upstanding from a surface thereof. Preferably, strap section 28 is a predetermined length of VELCRO ® brand hook fastener tape. The opposite surface of strap section 28 shown in a partial cutaway in FIG. 1 contains an adhesive material coating 32 which permits securing strap section 28 to at least a portion of the surface of a medical device such as a catheter tube 34. As shown in FIG. 1, strap section 28 is encircled about the catheter tube 32 in such a manner that the adhesive surfaces contact each other. Since such catheter tubes are generally constructed of silicone rubber—a material which is not easily adhered to—a positive attachment is provided to maintain the catheter tube 34 in a secured and fixed relation relative to the patient's limb by pressing strap member 14 as tightly as possible around tube 34 resulting in the formation of depression 36 along the width of strap member 14 as shown in FIG. 1.

The strap section 28 is positioned adjacent the opposite end of strap section 16 so that the hook-like elements 30 of strap section 28 can matingly engage the loop-like elements 20 of strap section 16. Preferably strap section 28 has a width no greater than that of strap section 16. This assures that a firm attachment of the catheter tube 34 relative to first strap section 16 may be obtained.

When assembled as shown, the fastening device 10 is ready to be secured about a limb of a patient. As noted above, the lengths of first and second strap sections 16, 22 respectively, are suitably selected so as to permit strap section 16 to encircle a limb of a patient and to overlap strap section 28 sufficiently so that strap section 22 extends beyond the region of strap section 28. The strap section 22 is positioned so that its hook-like elements 24 engage the loop-like elements 20 of strap section 16 along portion "B" identified in FIG. 3.

Figure 3A:
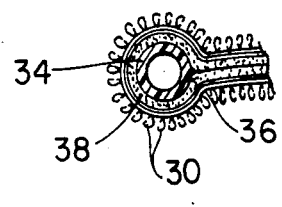
FIG. 3A is a view, partially in cross-section, of an alternate embodiment of the invention, utilizing an alternate strap section for securement to a catheter tube.

Referring now to FIG. 3A an alternative embodiment of the invention is illustrated. As shown in FIG. 3A the first strap section 16 is also constructed of a layer of polyurethane foam 38 which is attached to the rear surface of a third, hook-type strap section 28 so as to form a pad-like structure. In this instance, the adhesive material coating 32 is placed on the free surface of the foam layer 38 which is enveloped about the catheter 34. Strap section 16 in this embodiment is identical to the embodiment of FIG. 1. Thus the foam material of the first and third strap sections 16, 28 acts as a soft, but firm support having a friction surface which comfortably encompasses the limb and catheter tube 34 respectively and thereby prevents the catheter 34 from slipping out of its secured position relative to the limb. Since the foam surface is porous and breathable, the chances of producing ulcerations on an encircled human limb are minimized. The foam material also prevents the skin from chafing since it is breathable and resilient and it allows air to circulate to the skin, yet has sufficient frictional resistance and stretchability so as to firmly secure itself about the human limb. Furthermore, the cushioning property of the foam material prevents the constriction of the blood circulating through an encompassed limb, as well as preventing the crushing of the encircled catheter tube 34. In addition, the combination of the variable and precise fastening capabilities of the VELCRO ® brand fastener tapes with the cushioning characteristics of the foam material prevents constriction of blood flow through an encompassed leg or arm.

Referring once again to the FIGS., it can be seen that the free end portion "C" (shown in FIG. 1) of strap section 16 may be easily cut with a pair of scissors to reduce the size of the fastener 10. Advantageously, the various VELCRO ® brand hook fastener tapes are positioned such that the hook-type elements are disposed generally away from the free end portion "C" of first strap section 16 and these features facilitate the cutting of first section 16 to accommodate the broad range of human limb sizes from patient to patient and from arm sizes to leg sizes.

Referring now to illustration FIGS. 2 and 3, the fastening device 10 is secured to the thigh of a patient and supports thereto, a catheter tube 34. The catheter tube 34 is shown secured and supported by strap section 28 which itself is secured by overlapped portions of strap section 16 as previously described. The strap section 16 encircles the thigh as an endless loop as shown, and strap section 22 is releasably attached to the strap section 16. The unique construction and configuration of the present invention thereby prevents the catheter tube 34 from riding up, down, or sliding across the patient's thigh. Thus, the painful movement of an unsecured catheter tube 34 is easily and economically eliminated by the present invention. In addition, it has been found that the gentle and firm support provided for the catheter tube 34 is such that it is capable of maintaining the tube in traction where this may be required.

Figure 4:
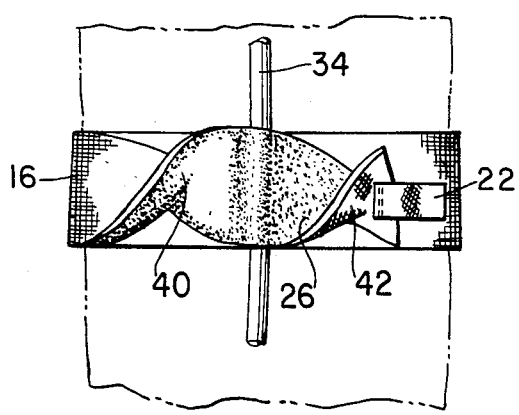
FIG. 4 is a view of the separable fastening device of the invention, illustrating an alternate technique for securing a catheter tube to a patient's leg.

In a second embodiment of the fastening device 10 as shown in FIG. 4, strap section 16 is successively folded over upon itself at locations 40 and 42 such that the strap portion between the folds 40 and 42 overlays the catheter tube 34. This configuration assures a firmer securement of the catheter tube 34. This extra securement is possible not only because of the twisted configuration of strap section 16, but particularly because the loop-type hooking surface of strap section 16 is now positioned to be attached to the hook-type hooking surface of strap section 28, as well as to the overlayed portion of strap section 16.

A fastening device 10' is shown in FIGS. 5–7 which is similar to the fastening device 10 of FIGS. 1–3. For the purpose of the description, similar components will be identified with like primed numbers and have the same function and structure as described above with respect to fastening device 10. As shown in FIG. 6, the fastening device 10' is adapted to support an intravenous (I.V.) tube 44 about an arm of a patient. For this reason, a significant difference between the fastening devices 10 and 10' is primarily one of size. The intravenous tube 44 is connected at its free end by means of a needle (not shown) to an arm of a patient. The other end of intravenous tube 44 is adapted to be inserted into a hub 46 which at its other end is connected to a feed tube 50. The feed tube 50 (usually constructed of silicone rubber) can be connected, e.g., to a source of fluid such as a plasma, glucose, or any other fluid which must be administered to the patient. The third strap section 28' is dimensioned so as to encircle the hub 46 above the shoulder 48 thereof. The adhesive material coating 32' assures a secure attachment of strap section 28' to hub 46. As shown in FIG. 5, a portion of the adhesive surface can be left exposed so as to permit adhesive adhering to the free surface of foam layer 26'. Also, as shown in FIG. 5, the self adhering portions of the third section 28' can be positioned closer to the end portion C' than as shown in similar FIG. 1.

As demonstrated in the above description, although the present fastener device 10 or 10' is preferably adapted to support medical tubes of various types such as catheter or intravenous tubes, it should be understood that the unique arrangement of the invention is readily adaptable to support any object to either a portion of a human body or a structural member in various configurations without departing from the scope of the invention. For example, in FIG. 8, the fastening device 10 is shown securing an electrode pick-up 52 to a portion of a body of a patient. Such electrode pick-ups are used in connection with electrocardiogram (EKG) diagnosis procedures to obtain electrical signals. In FIG. 8, wherein parts similar to those in FIG. 1 are identified by like double-primed numbers, strap section 28" is adhered only to the free surface of the electrode 52, leaving the underside free to contact the patient's body. The loop-type hooking surface of the first section 16" is positioned in matingly engaged relation with the hook-type hooking surface of the third section 28" and thereafter twisted at portion "D" by folding onto itself so as to expose a loop-type hooking surface for engagement with the hook-type elements 24" of the second section 22".

From the foregoing description it will be appreciated that the present invention is adaptable to numerous other fastener applications which will be readily foreseen by those skilled in the art. For example, the present fastener is suitable for use as noted above in EKG straps, I.V. tube straps, and also in wrist and ankle restraints, arm slings, anesthetic gas delivery hose straps, conduit or cable supports, flower pot hangers, utensil or pencil holders for handicapped persons, structural devices, etc. While other types of straps may be used for the above applications, it has been found that the unique configuration of the present invention makes it possible to firmly secure and support delicate members relatively inexpensively and avoid any real or potential disadvantages of crushing these members. Furthermore, as can be seen from the foregoing, the supporting and securing is accomplished in an improved manner notwithstanding the fact that the members to be secured have irregular, nonconforming configurations. Moreover, the first strap member is reusable which feature makes use of the fastening device 10 economical as well.

It will also be understood that the separable fastening device may be constructed of VELCRO ® brand hook and loop-type fastener straps in which the straps exhibit flexible, elastic properties in at least one direction. Such fastener tapes may be fabricated from elastic material such as natural or synthetic rubber or rubber based yarn, generally in the warp direction so as to provide elasticity at least along the length of the fastener tape.

I claim:

1. A separable fastening device adapted to support a catheter tube in adjacent relation to a portion of a human body such as a limb which comprises:
   a. a first flexible elongated strap section having:
      (1) a layer of foam material substrate; and
      (2) a textile material of knitted multifilamentary yarns having a multiplicity of loop-type filamentary engaging elements upstanding from a surface thereof, an opposite surface of said textile material being secured to one surface of said foam substrate, said foam substrate and textile materials having at least one tapered end portion;
   b. a second flexible strap section having a plurality of hook-type engaging elements upstanding from one surface opposite said first strap surface bearing loop-type elements and secured to the tapered end portion of said first strap section, said second strap section being configured and dimensioned for overlapping at least a portion of said first strap section and such that said hook-type engaging elements of said second strap section engage said loop-type engaging elements of said first strap section at a portion of said first strap section; and
   c. a third flexible strap section having an adhesive coating material on one surface capable of adhering to at least a portion of the surface of the catheter tube and a multiplicity of hooking elements of the hook-type upstanding from the other surface, said third strap section adapted so that a central portion of said one surface can adhesively encompass the catheter tube with said remaining end portions being adhered together, said hook-type element bearing surface of said third strap section adapted to be placed in selective detachable engagement with said loop-type element bearing surface of said first strap section so as to maintain said catheter tube in a substantially fixed relation with respect to said first strap section, and such that said first strap section can be positioned in surrounding relation about the third strap section encompassing the catheter tube to be supported, said surrounding relationship being retained by engagement of said respective engaging surfaces of said respective strap sections.

2. The separable fastening device according to claim 1 wherein said first strap section is twisted by folding over onto itself at locations adjacent before and after being positioned in surrounding relation about said third strap section encompassing the catheter tube.

3. A catheter tube support comprising:
   a. a first flexible strap member including:
      (1) a first strap section being generally tapered at one end and including a strap of multifilament yarn textile material having a plurality of loop-type resilient engaging hooking elements of knitted multifilament yarn material upstanding from one surface and a polyurethane foam material substrate secured to an opposite surface; and
      (2) a second flexible strap section of a woven or knitted nylon base material having a plurality of mating hook-type resilient engaging hooking elements upstanding from a surface opposite said surface of loop-type hooking elements of said first strap section, said second strap section being connected at one end to said generally tapered end of said first strap section; and
   b. a second flexible strap member including a third strap section of a woven or knitted nylon base material having an adhesive coating material on one surface thereof, and a plurality of mating hook-type resilient engaging hooking elements upstanding from an opposite surface thereof, said third strap section adapted to be adhesively secured about a portion of the catheter tube and selectively detachably matingly engaged to a surface portion of said first strap section at a location spaced from the tapered end such that encircling said first strap section about a human limb and overlapping said first strap section over said third strap section permits engagement of said hook-type hooking elements of said second strap section with said loop-type hooking elements of said first strap section to secure said catheter tube in relation to said limb.

4. A separable fastening device adapted to support a first member on a second member comprising a first strap section having a plurality of engaging elements upstanding from a first surface thereof, a second strap section connected to and extending from said first strap section and having a plurality of mating engaging elements upstanding from a surface opposed to said first surface of said first strap section, said second strap section capable of being positioned opposite said first surface of said first strap section such that the respective mating engaging elements may be placed in mating engaged face-to-face relation, a third strap section having adhering means on a first surface portion thereof and a plurality of engaging elements upstanding from an opposite surface thereof and capable of being selectively detachably positioned in mating engaged relation with said engaging elements of said first surface of said first strap section, said third strap section being dimensioned such that said adhering surface can be positioned in secured engaged adhered relation with at least a portion of the surface of the first member and adhered thereto so as to securely encompass at least a part thereof prior to mating engagement of said third strap section with said first strap section such that said first strap section may be positioned about said first member and said third strap section and the respective mating engaging elements placed in engaged relation so as to support the first member on the second member.

5. A separable fastening device adapted to support a first member such as a catheter tube or the like on a second member comprising a first and a second strap member, said first strap member including a first flexible strap section having a plurality of engaging elements upstanding from a first surface thereof, a second flexible strap section connected to and extending from said first strap section and having a plurality of mating engaging elements upstanding from a surface opposed to said first surface of said first strap section, said second strap section capable of being positioned opposite said first surface of said first strap section such that the respective mating engaging elements may be placed in mating engaged face-to-face relation, said second strap member including a third strap section having adhering means on a first surface portion thereof and a plurality of engaging elements upstanding from an opposite surface thereof and capable of being selectively detachably positioned in mating engaged relation with said engaging elements of said first surface of said first strap section, said third strap section being dimensioned such that said adhering surface can be positioned in secured engaged adhered relation with at least a portion of the surface of the first member and adhered thereto so as to securely encompass at least a part thereof prior to mating engagement of said third strap section with said first strap section such that said first strap section may be positioned about the first member and said third strap section and the respective mating engaging elements placed in engaged relation so as to support the first member on the second member.

6. A separable fastening device adapted to support a medical device such as an elongated catheter tube or the like on a support member comprising a first and a second strap member, said first strap member including a first flexible strap section having a plurality of resilient engaging elements upstanding from a first surface thereof, a second flexible strap section connected to and extending from said first strap section and having a plurality of resilient mating engaging elements upstanding from a surface opposed to said first surface of said first strap section, said second strap section capable of being positioned opposite said first surface of said first strap section such that the respective resilient mating engaging elements may be placed in mating engaged face-to-face relation, said second strap member including a third strap section having adhering means on a first surface portion thereof and a plurality of resilient engaging elements upstanding from an opposite surface thereof and capable of being selectively detachably positioned in mating engaged relation with said engaging elements of said first surface of said first strap section, said third strap section being dimensioned such that said adhering surface can be positioned in secured engaged adhered relation with at least a portion of the surface of the medical device and adhered thereto so as to securely encompass at least a part thereof prior to mating engagement of said third strap section with said first strap section such that said first strap section may be positioned about said medical device member and said third strap section and the respective mating engaging elements placed in engaged relation so as to support the medical device on the second member.

7. The separable fastening device according to claim 6 wherein at least one of said strap sections comprises at least one of a woven and knitted base material.

8. The separable fastening device according to claim 7 wherein said base material comprises at least one of a woven and knitted nylon material.

9. The separable fastening device according to claim 8 wherein at least one of said strap sections is comprised of a textile material having a plurality of resilient engaging elements upstanding from one surface and a foam material substrate secured to an opposite surface.

10. The separable fastening device according to claim 9 wherein said foam material substrate is polyurethane foam.

11. The separable fastening device according to claim 10 wherein said textile material comprises a strip of multifilament yarn textile material.

12. The separable fastening device according to claim 11 wherein said engaging elements are in the form of resilient loop-type hooking elements upstanding from said first surface portion of said first strap section and said mating engaging elements are in the form of resilient hook-type hooking elements upstanding from said surface of said second strap section opposite said first surface portion of said first strap section.

13. The separable fastening device according to claim 12 wherein said mating engaging elements upstanding from said opposite surface of said third strap section are in the form of resilient hook-type hooking elements.

14. The separable fastening device according to claim 13 wherein said strap sections are joined by engagement of said loop-type hooking elements with said mating hook-type hooking elements such that said loop-type hooking elements of said first strap section and said hook-type hooking elements of said second strap section and said third strap section face in opposite directions respectively.

15. The separable fastening device according to claim 14 wherein said resilient loop-type hooking elements comprise a knitted multifilament yarn material.

16. The separable fastening device according to claim 15 wherein said third strap section is detachably joined to the yarn material at a location spaced from said second end portion of said first strap section.

17. The separable fastening device according to claim 16 wherein said third strap section is disposed generally adjacent the joined portions of said first and second strap sections.

18. The separable fastening device according to claim 17 wherein said adhering means is an adhesive coating.

19. The separable fastening device according to claim 18 wherein said adhesive coating is pressure-sensitive.

20. The separable fastening device of claim 19 wherein said first and second strap sections are generally rectangular, said first strap section having a length substantially greater than said width.

21. The separable fastening device of claim 20 wherein said third strap section is generally rectangular having a width approximately equal to the width of said first strap section.

22. The separable fastening device of claim 21 wherein said third strap section is capable of being detachably joined to said first surface of said first strap section such that their respective widths are substantially aligned.

23. The separable fastening device of claim 22 wherein said first end portion of said first strap section has a generally tapered configuration having an end width approximately equal to the width of said second strap section.

24. The separable fastening device of claim 23 wherein said first and second strap sections are capable of being detachably joined at their respective end portions such that their respective widths are substantially aligned.

25. The separable fastening device according to claim 23 wherein said first and second strap sections are ultrasonically welded together at respective end portions of said first and second strap sections together.

26. A fastener for supporting an object on a support member comprising first, second, and third strap sections, said first strap section being provided on one surface with a multiplicity of loop-type hooking elements upstanding therefrom, and having a foam material substrate secured to the opposed surface, said second strap section being provided on one surface with a multiplicity of hook-type hooking elements upstanding therefrom, said second strap section being connected to and extending from said first strap section such that the hooking element surfaces of said first and second strap sections are opposite each other, said third strap section being provided on one surface with an adhesive coating, and on the other surface with a multiplicity of hook-type hooking elements upstanding therefrom, said third strap section being dimensioned such that at least a portion of said adhesive surface can be positioned contiguously in relation to at least a portion of said object, said object being retained in secured fixed relationship relative to said first and second strap sections upon engagement of at least a portion of said hook-type hooking elements of said third strap section with at least a portion of said hooking element surface of said first strap sections.

27. The fastener according to claim 26 wherein said third strap section comprises a generally rectangular flexible pad.

* * * * *